United States Patent [19]

Beedle et al.

[11] Patent Number: 4,981,866

[45] Date of Patent: Jan. 1, 1991

[54] ANTICONVULSANT AGENTS

[75] Inventors: Edward E. Beedle, Indianapolis; David W. Robertson, Greenwood, both of Ind.

[73] Assignee: Eli Lilly and Company, Indianapolis, Ind.

[21] Appl. No.: 499,878

[22] Filed: Mar. 27, 1990

Related U.S. Application Data

[62] Division of Ser. No. 335,393, Apr. 10, 1989, Pat. No. 4,939,163, which is a division of Ser. No. 16,047, Feb. 18, 1987, Pat. No. 4,835,181.

[51] Int. Cl.$^5$ ............... A61K 31/415; A61K 31/165
[52] U.S. Cl. .................................. 514/399; 514/618; 514/619; 514/620; 514/622
[58] Field of Search ................... 514/618, 619, 399

[56] References Cited

U.S. PATENT DOCUMENTS

| | | | |
|---|---|---|---|
| 4,004,029 | 1/1977 | Collins et al. | 424/325 |
| 4,305,940 | 12/1981 | Quadro | 424/248.54 |
| 4,379,165 | 4/1983 | Clark | 424/324 |
| 4,386,031 | 5/1983 | Hilboll et al. | 260/404 |
| 4,629,740 | 12/1986 | Robertson | 514/620 |
| 4,638,014 | 1/1987 | Clark | 514/619 |
| 4,642,379 | 2/1987 | Beedle et al. | 564/155 |

FOREIGN PATENT DOCUMENTS 1198019  7/1970  United Kingdom .

OTHER PUBLICATIONS

Hodd et al., *British Polymer Journal*, 15, 201 (1983).
Stout et al., *J. Med. Chem.*, 28, 295 (1985).
Rodriguez-Salazar, *J. Pharm. Sci.*, 63, 158 (1974).
Goerdeler et al., *Chem. Ber.*, 110, 2996 (1977).
Grammaticakis, *Bull. Soc. Chim. France*, 924 (1964), (CA 61:5488a).
Grammaticakis, *Bull. Soc. Chim. France*, 862 (1963), (CA 59:5945f).

*Primary Examiner*—Glennon H. Hollrah
*Assistant Examiner*—Brian Bembenick
*Attorney, Agent, or Firm*—Robert A. Conrad; Leroy Whitaker

[57] ABSTRACT

This invention provides certain 4-substituted benzamide derivatives, their pharmaceutical formulations, and their use as anticonvulsant agents.

6 Claims, No Drawings

ANTICONVULSANT AGENTS

This application is a division of application Ser. No. 07/335,393, filed Apr. 10, 1989, now U.S. Pat. No. 4,939,163 which is a division of application Ser. No. 07/016,047, filed Feb. 18, 1987, now U.S. Pat. No. 4,835,181.

BACKGROUND OF THE INVENTION

The several anticonvulsant drugs marketed in the United States provide significant seizure relief for only 50–75% of epileptic patients. The therapeutic effects are sometimes accompanied by serious side effects such as sedation, ataxia, psychoses, suicidal depression, gastrointestinal disturbances, gingival hyperplasia, lymphadenopathies, megaloblastic anemias, hepatotoxicity, nephropathies, hirsutism, and fetal malformations. These side effects, which range in severutt from mild sedation to death from aplastic anemia, are particularly troublesome since most of the marketed anticonvulsants have very low therapeutic ratios. For example, phenytoin, one of the most widely used anticonvulsants, controls seizures in man only when plasma levels reach 10 mcg/ml. Toxic effects such as nystagmus are seen at around 20 mcg/ml, ataxia is obvious at 30 mcg/ml, and lethargy is apparent at about 40 mcg/ml. See "The Pharmacological Basis of Therapeutics" (Gilman, Goodman, and Gilman, ed., 6th Ed., MacMillan Publishing Co., Inc., New York, N.Y. (1980)), p. 455. In view of these facts, most epileptologists indicate there is a definite need for more selective and less toxic anticonvulsant drugs.

SUMMARY OF THE INVENTION

This invention provides p-substituted benzamides of the formula I

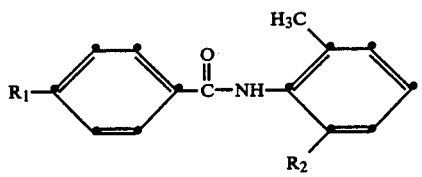

wherein
  $R_1$ is $-S(O)_p-(C_1-C_4$ alkyl), trifluoromethyl, aminomethyl, cyano, aminocarboxy, 1-imidazolyl, or $-NR_3R_4$, where $R_3$ and $R_4$ are independently $C_1-C_3$ alkyl, and
  $R_2$ is methyl, methoxy, trifluoromethyl, hydroxymethyl, or chloro;
and pharmaceutically acceptable acid addition salts thereof.

This invention also provides a method for treating and preventing convulsions in mammals in need of such treatment which comprises administering to said mammal an effective amount of a compound of the formula

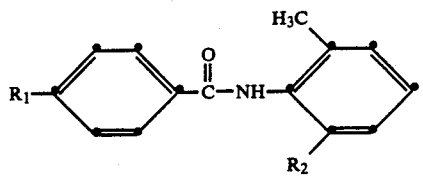

wherein
  $R_1$ is hydroxy, $C_1-C_4$ alkoxy, $-S(O)_p-C_1-C_4$ alkyl), trifluoromethyl, $C_1-C_4$ alkyl, aminomethyl, cyano, aminocarboxy, 1-imidazolyl, or $-NR_3R_4$, where $R_3$ and $R_4$ are independently $C_1-C_3$ alkyl, and
  $R_2$ is methyl, methoxy, trifluoromethyl, hydroxymethyl, or chloro;
and pharmaceutically acceptable acid addition salts thereof.

According to a further aspect of the present invention, there are provided pharmaceutical formulations which comprise as active ingredient a benzamide of formula II in association with a pharmaceutically acceptable carrier or diluent.

DETAILED DESCRIPTION OF PREFERRED EMBODIMENT

The present invention relates to organic compounds that are useful for treating and preventing convulsions in mammals.

The term "$C_1-C_4$ alkyl" refers to straight and branched aliphatic residues of one to four carbon atoms such as methyl, ethyl, propyl, isopropyl, t-butyl, and the like, and includes within it the term "$C_1-C_3$ alkyl".

The preferred compounds of this invention are those wherein $R_2$ is methyl and R is $-NR_3R_4$.

The pharmaceutically acceptable acid addition salts of this invention can be prepared by standard methods known in the art employing those acids of sufficient acidity to form acid addition salts of those compounds wherein $R_2$ is $-NR_3R_4$. These include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and di-carboxylic acids, phenyl-substituted alkanoic acids, hydroxy-alkanoic and -alkanedioic acids, aromatic acids, aliphatic and aromatic sulfonic acids, etc. Such pharmaceutically acceptable salts thus include sulfate, metaphosphate, pyrophosphate, chloride, bromide, iodide, fluoride, oxalate, maleate, benzenesulfonate, toluenesulfonate, chlorobenzenesulfonate, methanesulfonate, propanesulfonate, naphthalene-1sulfonate, naphthalene-2-sulfonate and the like. The Preferred salts are those derived from inorganic acids, especially hydrochloric acid.

Certain of the compounds of formula I and II can be prepared by standard acylation procedures well known in the art as summarized by the following scheme:

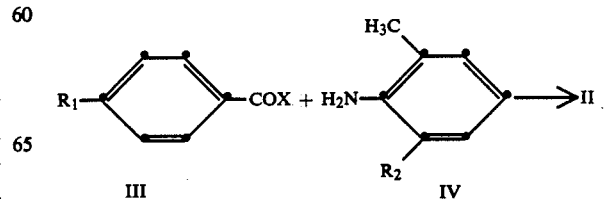

wherein X is bromo, chloro, or —OH.

Although any of a number of general acylation techniques may be employed, it is preferred that an acid halide (III, X is bromo or chloro) and the aniline (IV) be reacted in a nonreactive solvent, such as tetrahydrofuran or dimethylformamide, preferably in the presence of an acid scavenger such as a carbonate, especially potassium carbonate, or an organic base, such as triethylamine or pyridine. Although it is preferred that the reactants be added in the approximate molar ratio of about 1.25:1 (III:IV), other ratios are operative. The reaction is carried out from about room temperature up to the reflux temperature of the reaction mixture. Under the preferred conditions of approximately 25° C., the reaction is generally complete in 1–2 hours.

Standard coupling techniques employing carboxylic acids (III, X=—OH) may also be employed using coupling reagents such as DCC, EEDQ, CDI, etc.

The amino substituted compounds of this invention may also be prepared from the corresponding fluoro compound (i.e., a compound of general structure I or II except that $R_1$ is fluoro) by reacting with imidazole or an amine of the formula $R_3R_4NH$. In general, this reaction is accomplished by reacting a large excess of the amine with the fluoro intermediate, preferably in the presence of a non-reactive solvent such as dimethylsulfoxide, tetrahydrofuran, or the like. The reaction is generally carried out at temperatures from about 100–150° C. in a sealed reaction vessel. At the preferred reaction temperature of 150° C., the reaction is generally complete within approximately 18 hours.

Other compounds of the invention may also be derived from related compounds. For example, the nitrile compounds of this invention (I, $R_1$=—CN) may be transformed into the corresponding aminomethyl analogs (I, $R_1$=$H_2NCH_2$-) upon catalytic hydrogenation of the nitrile. Generally, this transformation is accomplished by hydrogenating the nitrile in a nonreactive solvent, such as tetrahydrofuran, in the presence of a catalyst, for example 5% palladium on carbon, until the theoretical amount of hydrogen has been consumed.

Similarly, the nitriles can be hydrolyzed to the corresponding carboxamide compounds of this invention (I, $R_1$=$H_2NCO$—). The preferred method of accomplishing this transformation involves heating the nitrile at reflux in an alcoholic solution of 3–4 equivalents of a strong base, such as sodium or potassium hydroxide. When employing the preferred alcohol t-butanol, the reaction is usually complete in about an hour.

The thio derivatives and intermediates of this invention (p is 0) may be transformed into the corresponding sulfoxide (p is 1) compounds upon treatment with a mild oxidizing agent, such as hydrogen peroxide in methanol, meta-chloroperbenzoic acid (MCPBA) in methylene chloride at 0° C., or an alkali metal periodate in aqueous alcohol. The corresponding sulfones (p is 2) are prepared from the thio or sulfoxide compounds on treatment with a strong oxidizing agent such as hydrogen peroxide in acetic acid or m-chloroperbenzoic acid in methylene chloride at 20–30° C.

The hydroxy compounds (II, $R_1$=OH) can be prepared from the corresponding methoxy derivatives by standard demethylation techniques. The preferred method comprises the use of boron tribromide in a nonreactive solvent such as methylene chloride as provided in Example 15 which follows.

The intermediates of Formulas III and IV and other necessary reagents for preparing the compounds employed in this invention are commercially available, are known in the art, or can be prepared by methods taught in the literature.

The p-substituted benzamides of Formula II are anticonvulsant agents and may be administered by various routes including the oral, rectal, transdermal, subcutaneous, intravenous, intramuscular, or intranasal routes, being usually employed in the form of a pharmaceutical composition. It is a special feature of these compounds that they are effective following oral administration. The invention includes a pharmaceutical composition comprising from about 1% to about 95% by weight of a p-aminobenzamide of Formula II, or a pharmaceutically acceptable acid addition salt thereof, associated with a pharmaceutically acceptable carrier.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions and sterile packaged powders.

Some examples of suitable carriers and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, methyl cellulose, methyl- and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient.

The compositions are preferably formulated in a unit dosage form, each dosage containing from about 5 to 500 mg, more usually 25 to 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.5 to 300 mg/kg of body weight. In the treatment of adult humans, the range of about 1 to 50 mg/kg, in single or divided doses, is preferred. However, it will be understood that the amount of the compound actually administered will be determined by a physician, in the light of the relevant circumstances including the condition to be treated, the choice of compound to be administered, the chosen route of administration, the age, weight, and response of the individual patient, and the severity of the patient's symptoms.

The following examples further illustrate the preparation of the intermediates, compounds, and formulations of this invention. The examples are illustrative only and are not intended to limit the scope of the invention in any way.

EXAMPLE 1

N-(2,6-dimethylphenyl)-4-(trifluoromethyl)benzamide

A solution of 25 g of 4-(trifluoromethyl)benzamide ride in tetrahydrofuran was added to 14.5 g of 2,6-dimethylaniline and 16.7 ml of triethylamine in tetrahydrofuran. The reaction was stirred at ambient temperature overnight, chilled, and filtered. The filtrate was evaporated in vacuo and the residue therefrom was dissolved in chloroform, washed sequentially with 1M hydrochloric acid, 1M sodium hydroxide, water, and a saturated sodium chloride solution, dried over sodium sulfate, filtered, and evaporated in vacuo. Crystallization from methanol provided the desired title product in 85% yield, m.p. 206–207° C.

Analysis for $C_{16}H_{14}F_3NO$:
Calculated: C, 65.52; H, 4.81; N, 4.78;
Found: C, 65.62; H, 4.97; N, 4.88.

EXAMPLES 2-5

The following benzamides were prepared from the appropriately substituted benzoyl chloride according to the procedure of Example 1.

2. 4-Cyano-N-(2,6-dimethylphenyl)benzamide, yield, m.p. 185–187° C.
Analysis for $C_{16}H_{14}N_2O$:
Calculated: C, 76.78; H, 5.64; N, 11.19;
Found: C, 76.84; H, 5.36; N, 11.11.

3. N-(2,6-dimethylphenyl)-4-methylbenzamide, yield, m.p. 163–164° C.
Analysis for $C_{16}H_{17}NO$:
Calculated: C, 80.30; H, 7.16; N, 5.85;
Found: C, 80.47; H, 7.02; N, 5.69.

4. N-(2,6-dimethylphenyl)-4-methoxybenzamide, 94% yield, m.p. 168–170° C.
Analysis for $C_{16}H_{17}NO_2$:
Calculated: C, 75.27; H, 6.71; N, 5.49;
Found: C, 75.15; H, 6.58; N, 5.19.

5. N-(2,6-dimethylphenyl)-4-(methylthio)benzamide, 76% yield, m.p. 183–185° C.
Analysis for $C_{16}H_{17}NOS$:
Calculated: C, 70.81; H, 6.31; N, 5.16; S, 11.82;
Found: C, 71.08; N, 6.48; N, 5.19; S, 11.99.

EXAMPLE 6

4-(Dimethylamino)-N-(2,6-dimethylphenyl)benzamide

A. Preparation of N-(2,6-dimethylphenyl)-4fluorobenzamide.

The subtitle intermediate was prepared in 68% yield from 4-fluorobenzoyl chloride following the procedure of Example 1, m.p. 180–181° C.
Analysis for $C_{15}H_{14}FNO$:
Calculated: C, 74.06; H, 5.80; N, 5.76;
Found: C, 73.83; H, 5.76; N, 5.76.

B. Preparation of 4-(dimethylamino)-N-(2,6dimethylphenyl)benzamide.

Ten grams of N-(2,6-dimethylphenyl)-4-fluorobenzamide were dissolved in 50 ml of dimethylsulfoxide in a high pressure/temperature bomb. Anhydrous dimethylamine (18.5 g) was added and the reaction vessel sealed and heated at 150° C. for 18 hours. The bomb was cooled and the contents poured into water. The mixture was extracted with chloroform. The organic layer was washed with water and a saturated sodium chloride solution, dried over anhydrous sodium sulfate, and concentrated in vacuo. The resulting residue was crystallized from methanol/water affording the desired title product in yield, m.p. 215–217° C.
Analysis for $C_{17}H_{20}N_2O$:
Calculated: C, 76.09, H, 7.51; N, 10.44;
Found: C, 75.85; H, 7.52; N, 10.15.

EXAMPLES 7-9

The following products were prepared according to the procedure of Example 6B employing the appropriate amine.

7. N-(2,6-dimethylphenyl)-4-(ethylamino)benzamide, 56% yield, m.p. 145–147° C.
Analysis for $C_{17}H_{20}N_2O$:
Calculated: C, 76.09; H, 7.51; N, 10.44;
Found: C, 75.86; H, 7.27; N, 10.14.

8. N-(2,6-dimethylphenyl)-4-(methylamino)benzamide, 35% yield, m.p. 163–164° C.
Analysis for $C_{16}H_{18}N_2O$:
Calculated: C, 75.56; H, 7.13; N, 11.01;
Found: C, 75.80; H, 7.18; N, 10.99.

9. N-(2,6-dimethylphenyl)-4-(methylpropylamino)benzamide, 49% yield, m.p. 159–160° C.
Analysis for $C_{19}H_{24}N_2O$:
Calculated: C, 76.99; H, 8.16; N, 9.45;
Found: C, 76.7S; H, 7.96; N, 9.29.

EXAMPLE 10

N-(2,6-dimethylphenyl)-4-(1H-imidazol-1-yl)benzamide hydrochloride

Imidazole (3.5 g) was dissolved in a small volume of dimethylformamide and added to a slurry of 1.81 g of 60% sodium hydride in oil in dimethylformamide. Five grams of N-(2,6-dimethylphenyl)-4-fluorobenzamide in a small volume of dimethylformamide was added to the reaction mixture. The reaction was heated at 100° C. for 18 hours, cooled, and poured into water. The mixture was extracted with ethyl acetate. The organic portion was washed with water and a saturated sodium chloride solution, dried over sodium sulfate, and concentrated in vacuo. The residue was chromatographed over silica gel eluting with an ethyl acetate and hexane gradient. The solvents of the combined appropriate fractions were removed in vacuo. The hydrochloride salt was generated by adding gaseous hydrogen chloride into a solution of the residue in ethanol. Crystallization of the recovered product from ethanol/ether provided the title product in 62% yield, m.p. 259–261° C.
Analysis for $C_{18}H_{17}N_3O \cdot HCl$:
Calculated: C, 65.95; H, 5.53; N, 12.82;
Found: C, 62.72; H, 5.34; N, 12.87.

EXAMPLE 11

4-(Aminomethyl)-N-(2,6-dimethylphenyl)benzamide hydrochloride

Ten grams of 4-cyano-N-(2,6-dimethylphenyl)benzamide were dissolved in 150 ml of tetrahydrofuran and hydrogenated over 5% palladium-on-carbon catalyst at 60 psi until the theoretical amount of hydrogen had been taken up. The catalyst was removed by filtration and the solvent evaporated in vacuo affording an oil. The oil was chromatographed over silica gel eluting with a methanol in methylene chloride gradient. The appropriate fractions were combined and concentrated in vacuo to provide a foam. The hydrochloride salt was generated by dissolving the foam in ethanol and bubbling in anhydrous hydrogen chloride gas. After evaporation, the hydrochloride salt was crystallized from ethanol affording the title product in 61% yield, m.p. 277–279° C.

Analysis for $C_{16}H_{18}N_2O\cdot HCl$:
Calculated: C, 66.09; H, 6.59; N, 9.63;
Found: C, 65.95; H, 6.62; N, 9.71.

EXAMPLE 12

N-(2,6-dimethylphenyl)-1-4-benzenedicarboxamide

Ten grams of 4-cyano-N-(2,6-dimethylphenyl)benzamide and 3 grams of finely powdered potassium hydroxide were slurried in t-butanol and heated at reflux for 50 minutes. The homogeneous mixture was poured into a saturated sodium chloride solution and extracted into chloroform. Material which was insoluable in both the organic and water phases was recovered by filtration, crystallized from methanol, and provided the title compound in 43% yield, m.p. 246–248° C.

Analysis for $C_{16}H_{16}N_2O_2$:
Calculated: C, 71.62; H, 6.09; N, 10.44;
Found: C, 71.33; H, 6.01; N, 10.38.

EXAMPLE 13

N-(2,6-dimethylphenyl)-4-(methylsulfinyl)benzamide

Ten grams of N-(2,6-dimethylphenyl)-4-(methylthio)benzamide were dissolved in a small volume of chloroform and chilled to 0° C. A solution of 7.9 g of m-chloroperoxybenzoic acid in chloroform was added in dropwise fashion. The reaction was stirred at room temperature for 1 hour, washed with a sodium bicarbonate solution, water, and a saturated chloride solution, dried over sodium sulfate and evaporated in vacuo. The resulting foam was chromatographed over silica gel eluting with an ethyl acetate in hexane gradient. The appropriate fractions were combined and the solvent removed in vacuo and the resulting residue was crystallized from ethyl acetate/hexane providing the desired title product in 59% yield, m.p. 144–146° C.

Analysis for $C_{16}H_{17}NO_2S$:
Calculated: C, 66.87; H, 5.96; N, 4.87;
Found: C, 67.10; H, 6.09; N, 4.77.

EXAMPLE 14

N-(2,6 dimethylphenyl)-4-(methylsulfonyl)benzamide

The title product was prepared in 86% yield following the procedure of Example 13 employing 7 g of the methylthiobenzamide and 10.6 g of m-chloroperoxybenzoic acid, m.p. 164–165.5° C.

Analysis for $C_{16}H_{17}NO_3S$:
Calculated: C, 63.34; H, 5.65; N, 4.62;
Found: C, 63.13; H, 5.71; N, 4.55.

EXAMPLE 15

N-(2,6-dimethylphenyl)-4-hydroxybenzamide

A solution of 6.4 g of N-(2,6-dimethylphenyl)-4-methoxybenzamide in methylene chloride was cooled to −75° C. Boron tribromide (25 g) was added over a 15 minute period. The reaction mixture was allowed to warm over 2 hours and then heated at reflux for 2 hours. The reaction was again cooled to −75° C. and 50 ml of water were added. The mixture was allowed to warm and the layers were separated. The organic layer was dried over sodium sulfate and evaporated in vacuo. The residue was crystallized from methanol/water affording the desired title product in 80% yield, m.p. 232–234° C.

Analysis for $C_{15}H_{15}NO_2$:
Calculated: C, 74.67; H, 6.27; N, 5.81;
Found: C, 74.39; H, 6.14; N, 5.58.

The following formulation examples may employ as active compounds any of the pharmaceutical compounds of the invention or their pharmaceutically acceptable salts.

EXAMPLE 16

Hard gelatin capsules are prepared using the following ingredients:

|  | Quantity (mg/capsule) |
|---|---|
| 4-Cyano-N-(2,6-dimethylphenyl)benzamide | 250 |
| Starch dried | 200 |
| Magnesium stearate | 10 |

The above ingredients are mixed and filled into hard gelatin capsules in 460 mg quantities.

EXAMPLE 17

A tablet formula is prepared using the ingredients below:

|  | Quantity (mg/tablet) |
|---|---|
| 4-(Dimethylamino)-N-(2,6-dimethylphenyl)benzamide | 250 |
| Cellulose, microcrystalline | 400 |
| Silicon dioxide, fumed | 10 |
| Stearic acid | 5 |

The components are blended and compressed to form tablets each weighing 665 mg.

EXAMPLE 18

An aerosol solution is prepared containing the following components:

|  | Weight % |
|---|---|
| N-(2,6-dimethylphenyl)-4-methoxybenzamide | 0.25 |
| Ethanol | 29.75 |
| Propellant 22 (Chlorodifluoromethane) | 70.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

EXAMPLE 19

Tablets each containing 60 mg of active ingredient are made up as follows:

| N-(2,6-dimethylphenyl)-4-(ethylamino)benzamide | 60 mg |
|---|---|
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50–60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 20

Capsules each containing 80 mg of medicament are made as follows:

| | |
|---|---|
| N-(2,6-dimethylphenyl)-4-(methyl-amino)benzamide sulfate | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 21

Suppositories each containing 225 mg of active ingredient are made as follows:

| | |
|---|---|
| N-(2,6-dimethylphenyl)-4-(methylpropylamino)benzamide | 225 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

EXAMPLE 22

Suspensions each containing 50 mg of medicament per 5 ml dose are made as follows:

| | |
|---|---|
| N-(2,6-dimethylphenyl)-4-hydroxybenzamide | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

The compounds of Formula II are anticonvulsant agents with a large therapeutic ratio and long half-life and are therefore useful in the treatment and prevention of convulsions in mammals. Moreover, the anticonvulsant compounds of this invention, in contrast to some anticonvulsant benzamides taught in the art, lack genetic toxicity and do not cause hemolysis. The compounds are effective against tonic extensor seizures elicited by maximal electroshock and should therefore be useful for treating generalized tonic-clonic ("grand mal"), cortical focal, complex partial (temporal lobe epilepsy), simple partial (focal motor), and post-traumatic seizures in humans. This activity is demonstrated in the electroshock induced convulsion inhibition assay which follows.

In the electroshock induced convulsion inhibition assay (E.S.), the compound to be tested was suspended in acacia and administered by gavage to each of ten Cox standard strain albino male mice (18–24 g) at the dose level being investigated. Thirty to 180 minutes after compound administration, the mice were subjected to a 0.1 second, 50 milliampere electroshock through corneal electrodes. The animals were examined and evaluated immediately after the electroshock for the occurrence of clonic, flexor tonic, or extensor tonic convulsions, or death and the $ED_{50}$ was determined for each compound as the dose which inhibited the occurrence of extensor tonic convulsions in one half of the animals immediately after the electroshock. For comparison, 18 milliamperes was usually sufficient to produce extensor tonic convulsions in about half of the control animals; at 50 milliamperes, almost all control animals (receiving vehicle only) died. The test results summarized in Table I are reported as the $ED_{50}$ values at the time interval found to provide an optimal response after dosing.

TABLE I

| Anti-convulsant Activity of compounds of Formula I | | |
|---|---|---|
| Example No. | Electroshock $ED_{50}$ (mg/kg)* | Time after dosing (minutes)** |
| 1 | ca. 225 | 60 |
| 2 | 13.2 | 60 |
| 3 | ca. 250 | 30 |
| 4 | 15 | 30 |
| 5 | ca. 75 | 180 |
| 6 | 3.65 | 120 |
| 7 | 2.45 | 60 |
| 8 | 2.0 | 120 |
| 9 | 4.6 | 120 |
| 10 | ca. 50 | 120 |
| 11 | 38 | 60 |
| 12 | ca. 75 | 60 |
| 13 | 13 | 60 |
| 14 | 14 | 60 |
| 15 | 11.2 | 60 |

*oral dose (gavage)-See text for methodology.
**Time (between dosing and administration of the electroshock) providing an optimal response.

We claim:

1. A method for treating or preventing convulsions in mammals in need of such treatment which comprises administering to said mammal an effective amount of a compound of the formula

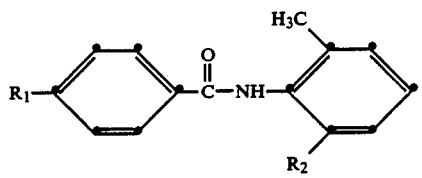

wherein
$R_1$ is hydroxy, $C_1$–$C_4$ alkoxy, -S(O)$_p$-($C_1$–$C_4$ alkyl), trifluoromethyl, $C_1$–$C_4$ alkyl, aminomethyl, aminocarboxy, 1-imidazolyl, or -NR$_3$R$_4$, where R$_3$ and $R_4$ are independently $C_1$–$C_3$ alkyl, P is 0, 1, or 2, and $R_2$ is methyl, methoxy, trifluoromethyl, hydroxymethyl, or chloro, or a pharmaceutically acceptable acid addition salt thereof.

2. The method of claim 1 employing a compound wherein $R_2$ is methyl.

3. The method of claim 2 employing a compound wherein, $R_1$ is -$NR_3R_4$.

4. The method of claim 3 employing the compound 4-(dimethylamino)-N-(2,6-dimethylphenyl)benzamide or a pharmaceutically acceptable acid addition salt thereof.

5. The method of claim 3 employing the compound N-(2,6-dimethylphenyl)-4-(ethylamino)benzamide or a pharmaceutically acceptable acid addition salt thereof.

6. The method of claim 3 employing the compound N-(2,6-dimethylphenyl)-4-(methylamino)benzamide or a pharmaceutically acceptable acid addition salt thereof.

* * * * *